United States Patent [19]
Kollhof et al.

[11] Patent Number: 6,075,880
[45] Date of Patent: Jun. 13, 2000

[54] METHOD FOR DETECTION OF DEFECTS IN THE INSPECTION OF STRUCTURED SURFACES

[75] Inventors: Dietmar Kollhof, Ilmenau; Joachim Wienecke, Jena; Karl-Heinz Franke, Ilmenau; Michael Graef, Jena; Heiko Kempe, Geraberg, all of Germany

[73] Assignee: Jenoptik Technologie GmbH, Jena, Germany

[21] Appl. No.: 08/395,668

[22] Filed: Feb. 28, 1995

[30] Foreign Application Priority Data

Mar. 16, 1994 [DE] Germany ............... P 44 10 603

[51] Int. Cl.[7] ................................................. G06K 9/00
[52] U.S. Cl. ......................... 382/141; 382/144; 382/147
[58] Field of Search ..................................... 382/141, 144, 382/145, 146, 147, 148, 149, 150, 151

[56] References Cited

U.S. PATENT DOCUMENTS

| | | |
|---|---|---|
| 4,477,926 | 10/1984 | Linger et al. |
| 4,961,231 | 10/1990 | Nakayama ........................... 382/21 |
| 5,008,946 | 4/1991 | Ando ..................................... 382/2 |
| 5,450,502 | 9/1995 | Eschbach ........................... 382/169 |
| 5,452,368 | 9/1995 | Le Beau ............................. 382/145 |
| 5,475,766 | 12/1995 | Tsuchiya ............................. 382/144 |
| 5,537,483 | 7/1996 | Stapleton ........................... 382/168 |
| 5,537,669 | 7/1996 | Evans et al. ....................... 382/141 |
| 5,579,402 | 11/1996 | Hayen ................................. 382/133 |
| 5,594,807 | 1/1997 | Liu ...................................... 382/168 |
| 5,596,654 | 1/1997 | Tanaka ................................ 382/168 |

FOREIGN PATENT DOCUMENTS

| | | |
|---|---|---|
| 0 475 454 A2 | 3/1992 | European Pat. Off. . |
| 0 574 831 A1 | 12/1993 | European Pat. Off. . |
| 41 33 590 | 1/1993 | Germany . |
| 2 150 284 | 6/1985 | United Kingdom . |
| 91/16619 | 10/1991 | WIPO . |

*Primary Examiner*—Dwayne Bost
*Assistant Examiner*—Brian L Johnson
*Attorney, Agent, or Firm*—McAulay Fisher Nissen Goldberg & Kiel, LLP

[57] ABSTRACT

The object of a method for detecting defects in the inspection of structured surfaces is to ensure a detection of defects which is not dependent on the number of structuring planes and includes structure features in real-time operation for separating defects from good structures. From image point classification in which zones of a recorded image which have similar image point features are assembled, a grayvalue intermediate image containing edge structures and corner structures is generated from the image and the behavior of the image point features of every image point in the intermediate image is analyzed with respect to its neighboring image points. The method is used predominantly in statistical process control in the production process of masks, LCD's, printed circuit boards and semiconductor wafers.

22 Claims, 6 Drawing Sheets

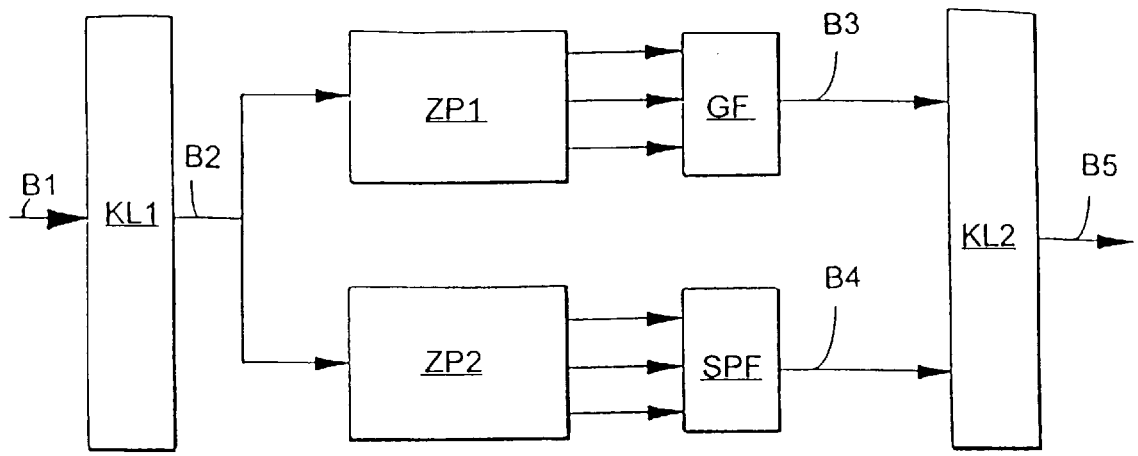
FIG. 11
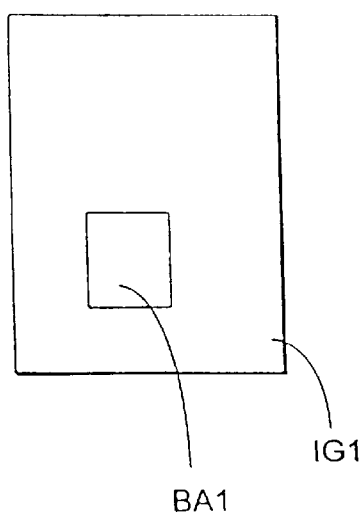 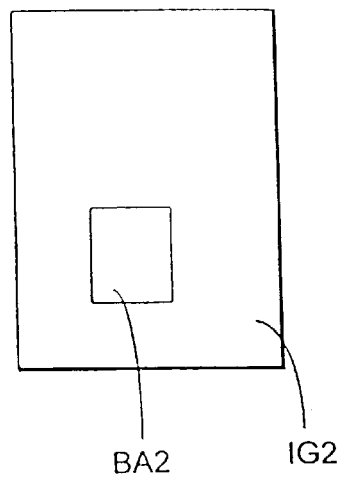
FIG. 12A  FIG. 12B

METHOD FOR DETECTION OF DEFECTS IN THE INSPECTION OF STRUCTURED SURFACES

BACKGROUND OF THE INVENTION a) Field of the Invention

The invention is directed to a method for detecting defects during the inspection of structured surfaces, in particular masks, LCD's, printed circuit boards and semiconductor wafers, using specific image point features of the structures and defects in a recorded image of the surface in which zones of the image having similar image point features are compiled by image point classification and the behavior of the image point features of an image point is analyzed with reference to its neighboring image points by structure classification. The method is used predominantly in statistical process control in the production process.

b) Description of the Related Art

There are a great many methods for mechanical inspection of surfaces provided with structures. These methods can basically be distinguished as follows:

light scattering or laser scan methods, holographic methods, digital image processing methods.

In digital image processing, there are two basic approaches in solving inspection problems. A first variant is based on a comparison of reference values with actual values which, in turn, comprises three distinct methods:

1. Image-image comparison: the reference image is supplied by a test sample.
2. Image-data comparison: the reference image is supplied by an image synthesized from the CAD data record.
3. Data-data comparison. The comparison of reference values to actual values is effected on the basis of the CAD data.

Depending on the procedure, the effective principles of the first two methods require an extremely accurate positioning of the object support, two absolutely identical opto-electronic image channels and an extremely precise synthesis of sample images taking into account all physical and technical characteristics including tolerances ranging from illumination over the object, optical imaging, signal conversion in the sensor, analog channel to the virtual image.

In the third method, a complete analysis of the real image is required, i.e., in processing real-time images, trouble-free segmentation of the image, edge detection, approximation of structure elements and the description of the setting must likewise be achieved in real time.

All of the above-mentioned solutions based on comparison of actual and reference values are very cost-intensive due to the extremely high technical requirements for optics, precision mechanics, state detection and electronics (reference image generator).

On principle, these solutions can be used only for binary structures (masks, LCD's), lower structuring planes of process wafers and for comparison between simple repetitive structures.

In higher technological layers of the wafer, the characteristics of the layers and structure edges change due to technological processing and by overlapping and overlaying in such a way that the uncertainties in this area can no longer be overcome by comparing reference and actual values.

This manifests itself particularly with respect to changes in thickness in the individual layers (they lead to changes in grayscale value and color) and in overlay tolerances. All of these technological peculiarities add to the difficulty of comparison of reference values and actual values or render such comparison impossible. In addition, polysilicon and metallization layers are imaged as textured regions by means of statistical model parameters so that they are likewise inaccessible to comparison methods. Examples of such solutions are described in the patents mentioned in the following.

In an image-to-image comparison according to DE 2508992, an actual structure is compared with a second actual structure by means of split optical beam paths. The two images can also be superimposed on one another in the form of a video image and the combined image is then evaluated. In this method, structural defects are determined from mismatches in the covering of the two combined images.

In another method according to DE 2700252, the structure to be tested is raster-scanned by a test beam and broken up into image points. The total image which is digitized in this way is fed to a data processing system in which the scanned structure is compared with a reference image, reference structure or structure rules contained in a storage.

EP 0426 182 discloses a combined method which describes the generally known image-image comparison of two adjacent control objects on the one hand and the image-image comparison on a control object on the other hand. This method makes use of the fact that in certain classes of highly integrated circuits (storages, CCD arrays and other multielement sensors) structure elements are repeated on a chip many times.

Further examples for such a comparison of reference values to actual values are described in the following patents: DE 3336470, DE 3612268, DE 3714011, DE 4136830.

The second variant makes use of technological peculiarities by proceeding from a detection of defects on the basis of their specific features resulting from interference and deviations in the parameters of the technological processes, material defects, low-quality process materials, impurities and imperfections in the crystal structure.

In contrast to comparison testing, this direct detection of defects makes do, to a great extent, without extensive information on the reference structure, since it proceeds from determined fundamental rules or deviations from rules in detecting the image. Such rules and aberrations are provided substantially by color features and shape features of the reference structure, reference layer or defect.

One of these methods, described in DE Patent 3427981, proceeds from the fact that a minimum structure spacing can be defined on every structured control object and that a large number of the defects present on the control object have dimensions greater than or smaller than the given dimensions of the structure. Therefore, in an automatic inspection according to this patent, a measurement window can be used which measures a geometric structure as falling short of or exceeding the given structure dimensions.

Accordingly, these measurement windows detect only those structure elements lying within the given measurement window and not those which match the defined structure dimensions.

A disadvantage consists in that, in higher structuring planes of a wafer, a minimum spacing can no longer be defined by the technological peculiarities, in particular by overlaying different structure components, and the method is therefore only practicable for binary structures.

OBJECT AND SUMMARY OF THE INVENTION

Therefore, the primary object of the present invention is to ensure a detection of defects regardless of the number of structuring planes while taking into account structure features in real-time operation for separating defects from good structures.

According to the invention, this object is met by a method for detecting defects in the inspection of structured surfaces, in particular masks, LCD's, printed circuit boards and semiconductor wafers, using specific image point features of the structures and defects of a recorded image of the surface in which zones of the image having similar image point features are compiled by image point classification and the behavior of the image point features of an image point is analyzed with reference to its neighboring image points by structure classification, in that a gray-value intermediate image containing edge structures and corner structures and serving for structure classification is generated in the image point classification of the recorded image.

In generating the gray-value intermediate image containing edge and corner structures, defects are extensively separated from good structures in a pre-segmenting without introducing thresholds in that the image point classification is effected in a blurred, so-called fuzzied classification whose results do not contain any binary image with sharp separation characteristics.

In order to generate the intermediate image, distributions of image point features of selected random samples which correspond at least to the number of defect-free surface portions with distinct features are described in a first feature space plotted by the number of image point features by means of probabilities which, being transformed into grayscale values, are the contents of an addressable storage for revaluation of every image point feature of the recorded image into a grayscale value and the distributions of all random samples form an overall distribution.

The results of an evaluation of the surroundings for each image point of the intermediate image carried out on the basis of at least two uncorrelated characteristics are stored in a second addressable storage in binary form so as to be separated into defect-free regions and defect regions, wherein the size of the storage is determined by a second feature space plotted by the number of evaluated characteristics and the storing in the storage corresponds to the distribution of characteristics of every image point in the feature space.

Both the recorded image and the image contents which have already been stored are suitable for taking random samples.

In addition to the random samples of defect-free surface portions, random samples of surface portions with defects can also be used to generate the intermediate image.

Both small-area and large-area defects are detected by means of filtering the gray-value intermediate image and the sharp separation of defect zones and good zones which is carried out subsequently.

The evaluation of surroundings is effected by at least two filters with variable core and uncorrelated characteristics by means of noise suppression and highlighting self-contained zones lying within the evaluated surroundings.

It is advantageous to use a pair of filters, one of which is a low-pass filter, in particular a Gauss filter, and the other a bandpass filter, in particular a spot filter whose core is the second derivative of a two-dimensional Gaussian function.

The addressable storages are advantageously lookup tables. Color features of the image points, included grayscale values, as well as texture features associated with every image point by virtue of its surroundings, can be used as image point features. However, other multichannel information of the image points to be analyzed is also suitable.

Further, it is advantageous when an image section or cutout which corresponds to the dimensions of the recorded image and in which detected defects once again serve as random samples is first selected from a first inspection zone of different inspection zones in order to determine the contents of the first and second storage and the applicability of the results to at least one image cutout is tested in at least one of the other inspection zones.

Storage contents of the first and second storage representing characteristic primitive images can be contents of a database. This applies also for information concerning test structures and image data of good zones and defect zones. The contents of the database may be resorted to if necessary, in particular when checking the applicability of classifiers or when classifiers are to be corrected.

An embodiment example of the invention is explained more fully in the following with reference to the schematic drawings.

BRIEF DESCRIPTION OF THE DRAWINGS

In the drawings:

FIG. 11 shows a circuit arrangement for realizing the method according to the invention; and FIGS. 12A and 12B shows a model for an expanded method for determining the contents of the first and second storages.

DESCRIPTION OF THE PREFERRED EMBODIMENTS

Figure 1:
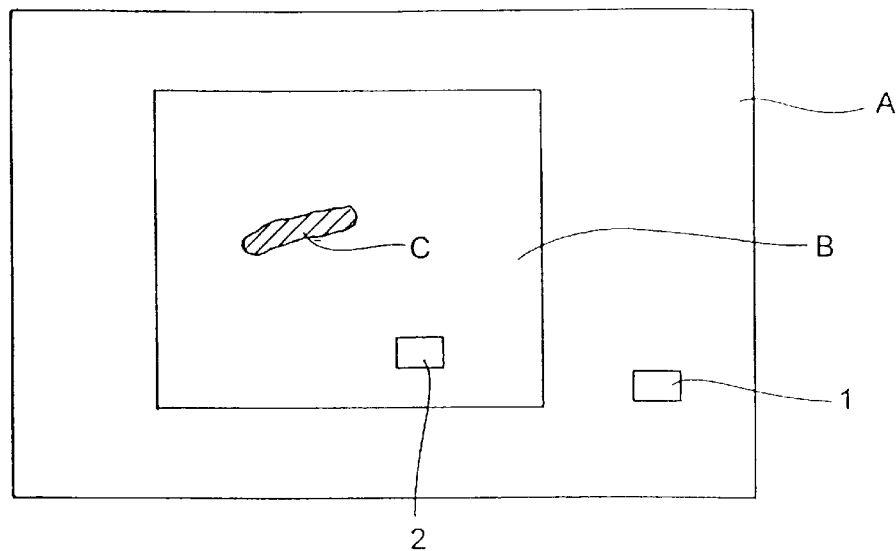
FIG. 1 shows an image of a structured surface.

The image cutout, shown in FIG. 1, from the surface of a semiconductor to be inspected contains good zones in the form of defined structures A and B and a detectable included defect C.

For the sake of simplicity, the embodiment example is directed to an image cutout containing only gray-value information, since evaluation of color images or texture images result in higher-dimensional spaces.

Figure 2:
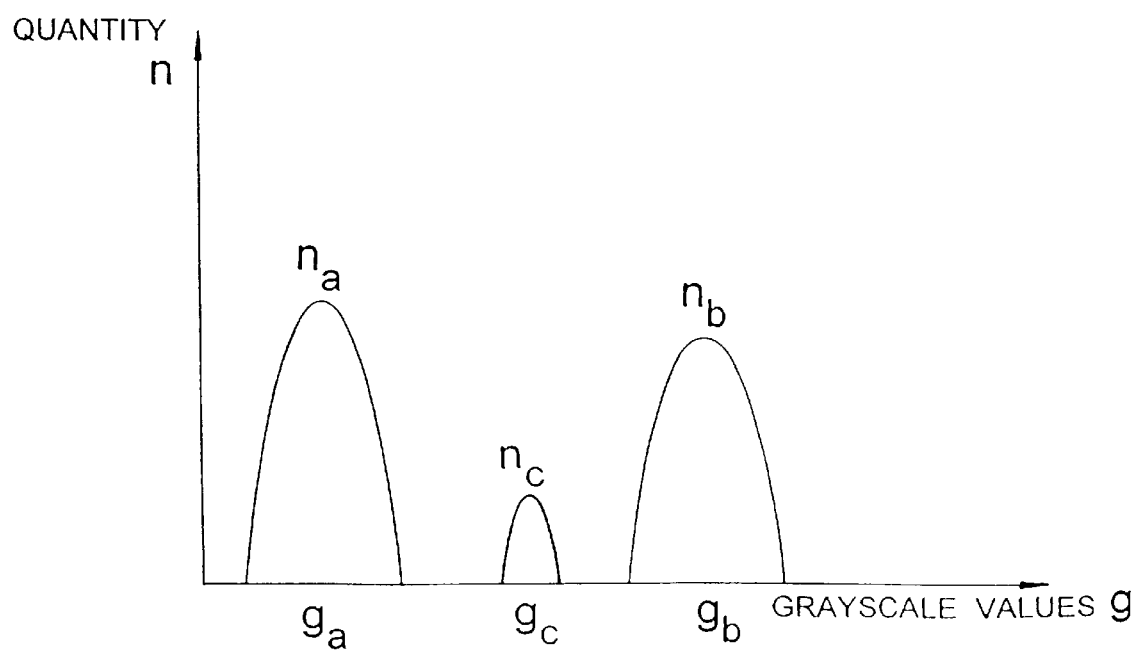
FIG. 2 shows the grayscale value distribution of the image according to FIG. 1.
Figure 3:
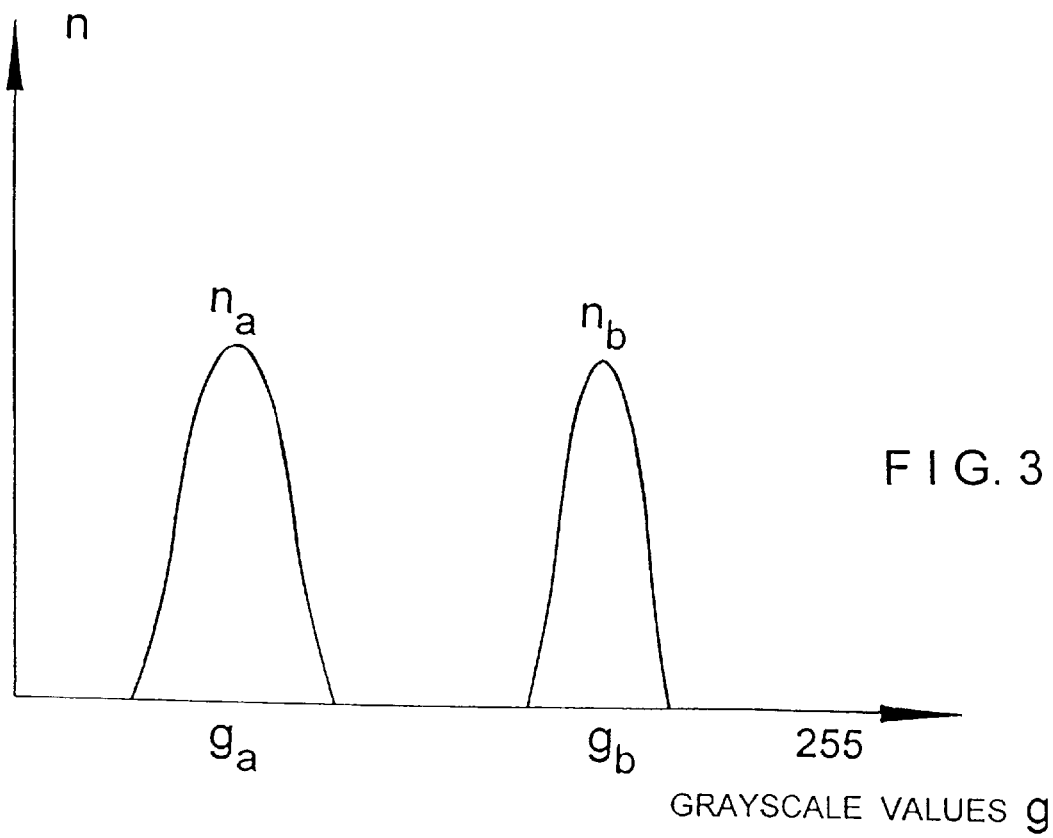
FIG. 3 shows histograms of selected random samples.

The grayscale value distribution of the image cutout in FIG. 2 contains grayscale value maxima $n_a$, $n_b$ and $n_c$ with mean grayscale values $g_a$, $g_b$ and $g_c$. In the method according to the invention, in which evaluation criteria are to be determined for the actual inspection, suitable random samples, designated by 1 and 2, are taken from structures A and B.

Image point features are grayscale values whose distributions are represented in a first one-dimensional feature space and which may justly be regarded as Gaussian distributions. Relative grayscale value maxima $n_a$ and $n_b$ associated with structures A and B occur at mean grayscale values $g_a$ and $g_b$.

In order to assign an image point to a class of good zones or defect zones, a probability which is proportional to the estimated probability density of the distribution of random samples in the feature space and which takes on the value 1 in the center of the distribution is assigned to every image point from the image cutout.

A probability $P_a(g)$ is given as a measurement for allocation to the grayscale value distribution of structure A and is determined by $$P_a(g) = e^{-(g-g_a)^2/2s_a^2},$$

where $g_a$ is estimated as mean value and $s_a$ is estimated as variance by the grayscale value distribution of the random sample from structure A.

This holds true in an analogous manner for probability $P_b(g)$:

$$P_b(g) = e^{-(g-g_b)^2/2s_b^2},$$

and for the probability $P(g)$ to belong to any one of the good zones, $$P(g) = 1 - [1 - P_a(g)] * [1 - P_b(g)].$$

Accordingly, image points with a grayscale value corresponding either to the mean value of the distribution of structure A or the distribution of structure B are allotted a probability of 1.

Figure 4:
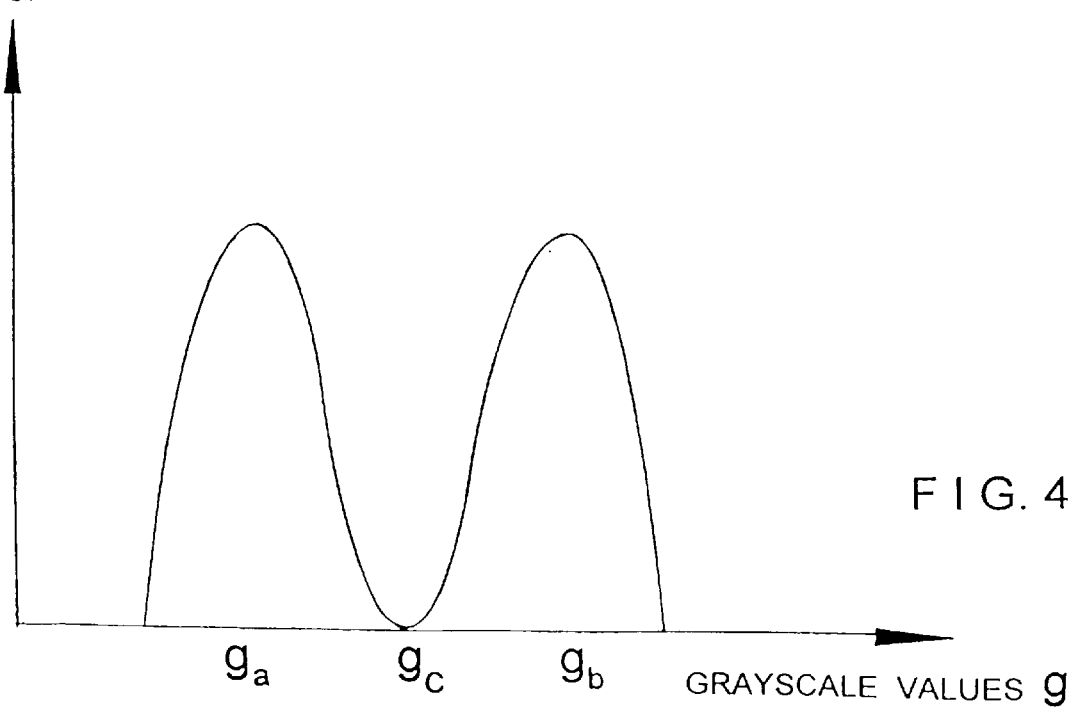
FIG. 4 shows a probability distribution of the grayscale values for random samples selected from the structured surface.

According to this method, all image points whose characteristics are very similar to any one of the good zones receive high probability values. The resulting probability distribution is shown in FIG. 4.

If function $P(g)$ is taken as a prescript for revaluating the grayscale values of the image cutout into new grayscale values, then, according to the invention, image points whose grayscale values come close to those of random samples A and B receive high grayscale values which decrease as the probability distance increases, so that image points from defect C are allotted low grayscale values without having to teach this defect C itself by means of random samples. Of course, it is also possible to teach the defect C "negatively" in addition by means of a random sample.

The new grayscale values f result from the equation $$f = f_{max} * P(g),$$

where $f_{max}$ represents the total number of possible grayscale steps.

An image point from FIG. 1 with grayscale value $g_a$ accordingly receives grayscale value $f_{max}$. This is equally true for an image point in FIG. 1 with grayscale value $g_b$. Since there are $n_a$ image points with grayscale value $g_a$ and $n_b$ image points with grayscale value $g_b$, according to the grayscale value distribution shown in FIG. 2, there are $(n_a+n_b)$ image points with grayscale value $f_{max}$.

The $n_c$ image points with grayscale value $g_c$, which describe the mean characteristics of defect zone C in FIG. 1, receive grayscale value $f_c$ by $$fc = f_{max} * [P_a(g_c) + P_b(g_c) - P_a(g_c)P_b(g_c)].$$

Figure 5:
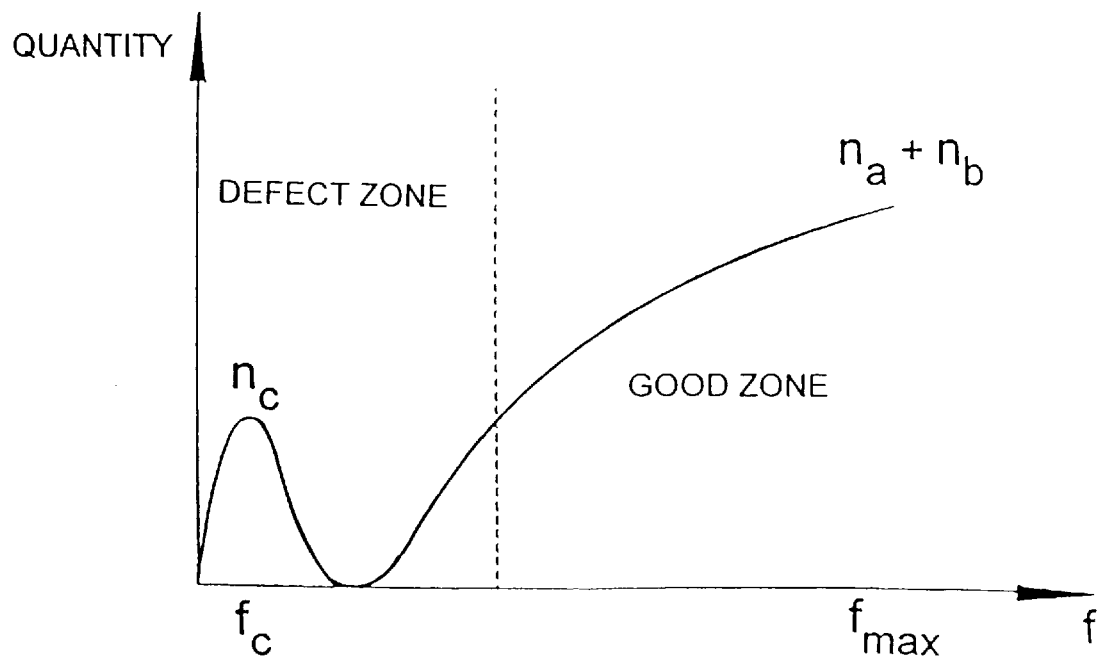
FIG. 5 shows the grayscale value distribution of an intermediate image generated from the image according to FIG. 1.

This situation is shown in FIG. 5.

Figure 6:
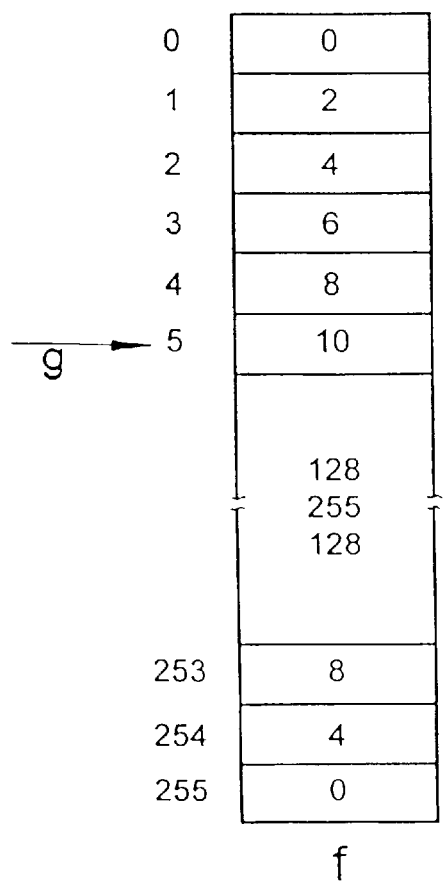
FIG. 6 shows new grayscale values entered in a lookup table.
Figure 7:
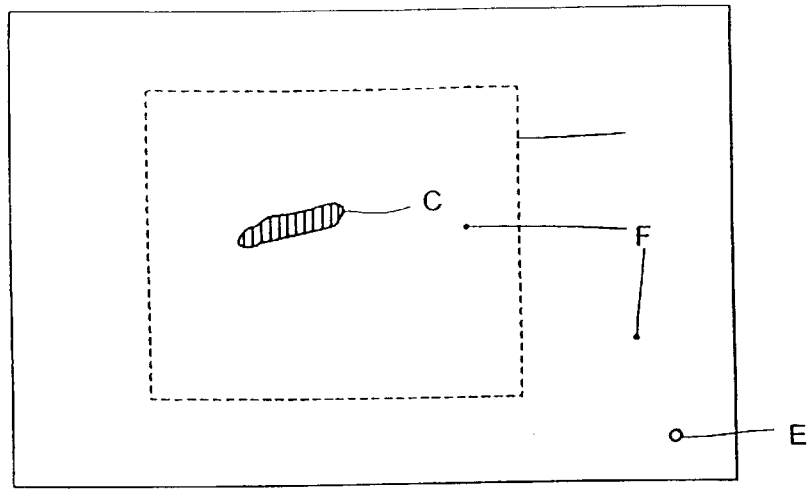
FIG. 7 shows the generated gray-value intermediate image.

As will be seen from FIG. 6, the new grayscale values of the random samples formed by revaluation are entered in an addressable storage in the form of a lookup table, so that it is now possible to transfer the image cutout into a probability image in the form of a gray-value intermediate image corresponding to FIG. 7.

Every grayscale value $g_{x,y}$ of an image point from FIG. 1 with coordinates x, y activates a "pointer" (represented by →) which is directed to the corresponding grayscale value in the lookup table. The converted grayscale value f in the corresponding storage cell is entered in the converted image with coordinates x', y'.

The lookup table is a first classifier for image point classification which substantially changes the image contents of FIG. 1 as will be seen from FIG. 7. The contents of the lookup table are used via a RAM during inspection due to the real-time requirements.

Naturally, by using the generated intermediate image according to FIG. 7, it can be detected directly whether or not the evaluating criteria determined in this way and realized in the classifier correspond to the given requirements. None of the good zones shown in FIG. 1 may appear dark in the gray-value intermediate image and the edge structures and corner structures must still be present. A software simulation of the lookup table can also be used in an advantageous manner.

By applying grayscale values, the individual image points were judged to belong to a good zone based on probability. Regardless of how many good zones are contained in an image cutout, the respective intermediate image always has a grayscale value distribution similar to that shown in FIG. 5 according to the first processing step which has been described thus far. Accordingly, the grayscale value distribution shown in FIG. 2 is successfully classed into defect zones and good zones according to FIG. 5 without introducing thresholds. The generation of the intermediate image as a so-called known image (zones of an initial image are made "known" in a teaching phase) is not limited to the information in the grayscale values of an image as is illustrated in this example for the sake of clarity. Color information as well as other information on texture or characteristics of image points in neighboring regions which delimits a feature space can also used for classification.

It will be seen with reference to the intermediate image in FIG. 7 that the problem of defect detection is not yet solved by this first processing step. Naturally, in the transitional zone from zone A to zone B in the edges, grayscale values occur which extend into the defect zone of the feature space. An additional zone D occurs in FIG. 7.

This is equally true of the ratios in a color or texture classification in which unavoidable color fringes which considerably interfere with a color evaluation occur due to diffraction and interference effects in the imaging of structure edges. In the edge regions, the color value proportions change to such an extent and in so complex a manner, depending on the focussing state, contrast ratios and difference in height between adjacent layers, that a simple defect detection by means of classification of color pixels leads to substantial pseudo-defect rates in the edge regions. Moreover, detection of micro-defects, shown in FIG. 7 as a punctiform object E, is critical since their dimensions lie in the order of magnitude of the width of edge transitions D.

Therefore, the local surroundings of the image points of the intermediate image are analyzed more extensively with respect to the features of good structures and defective structures in a second processing step.

Figure 8:
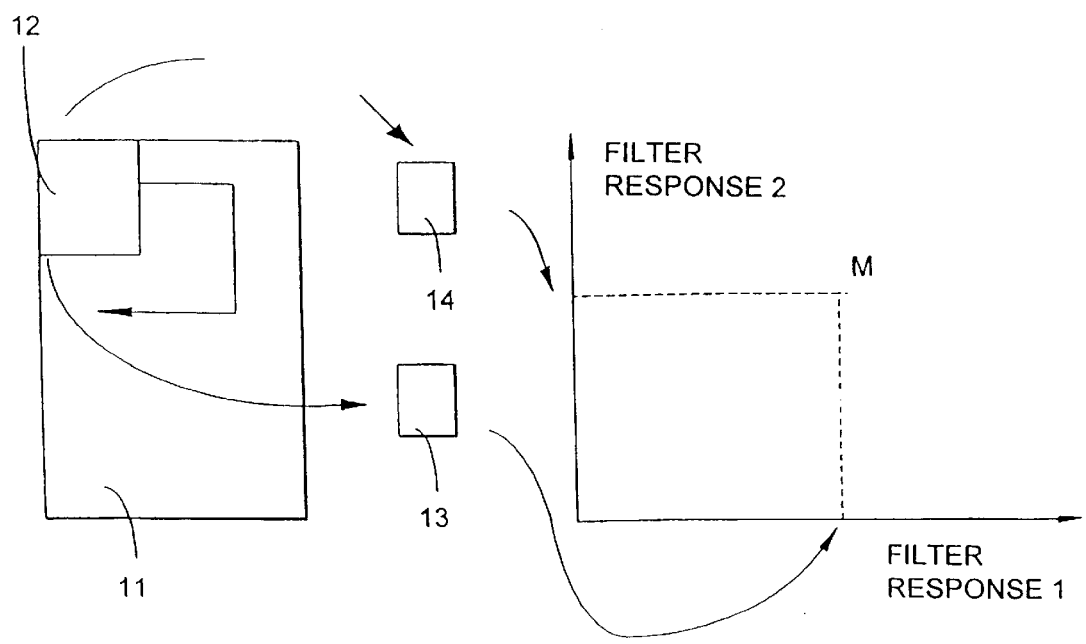
FIG. 8 shows an evaluating method for determining the behavior of the image point features of an image point in relation to neighboring image points for eliminating edge transitions and corner transitions and highlighting microdefects.

For this analysis, the intermediate image, designated by 11, is rastered point by point by a "window" 12 as will be seen from FIG. 8. As a result, existing local cutouts are evaluated with respect to their image contents by a filter 13 and by a filter 14 according to characteristics not correlated with one another. The results of the evaluation can be represented in the form of a filter response 1 and a filter response 2 as two coordinates in a two-dimensional feature space for every image point as point M. Point clouds occur, wherein local zones having identical characteristics, with reference to filters 13 and 14, form accumulation zones in the feature space without local association in the intermediate image.

The use of a Gauss filter for filter 13 for noise suppression and a spot filter for filter 14, whose core represents the second derivative of a two-dimensional Gaussian function, proves advantageous for highlighting self-contained zones (micro-defects) within the evaluated surroundings. By using these filters, it is possible to generate point clouds which are virtually free of correlation as will be seen from FIG. 9.

Zones A and B from FIG. 1, which correspond to zones F in FIG. 7, are imaged as highly known zones in a first point cloud 15 and structures D are imaged as a point cloud 16 in the immediate vicinity. Image point clouds for defect zones C and E are designated by 17 and 18.

Of course, it is also possible, depending on defect characteristics and the permissible rate of false alarms, to use a greater number of different filters, e.g., directional low-pass, bandpass and high-pass filters. Higher-dimensional feature spaces occur corresponding to the number of filters. The defect which is the subject of the search must be imaged as far as possible from the point clouds of the good zones in the feature space.

Figure 9:
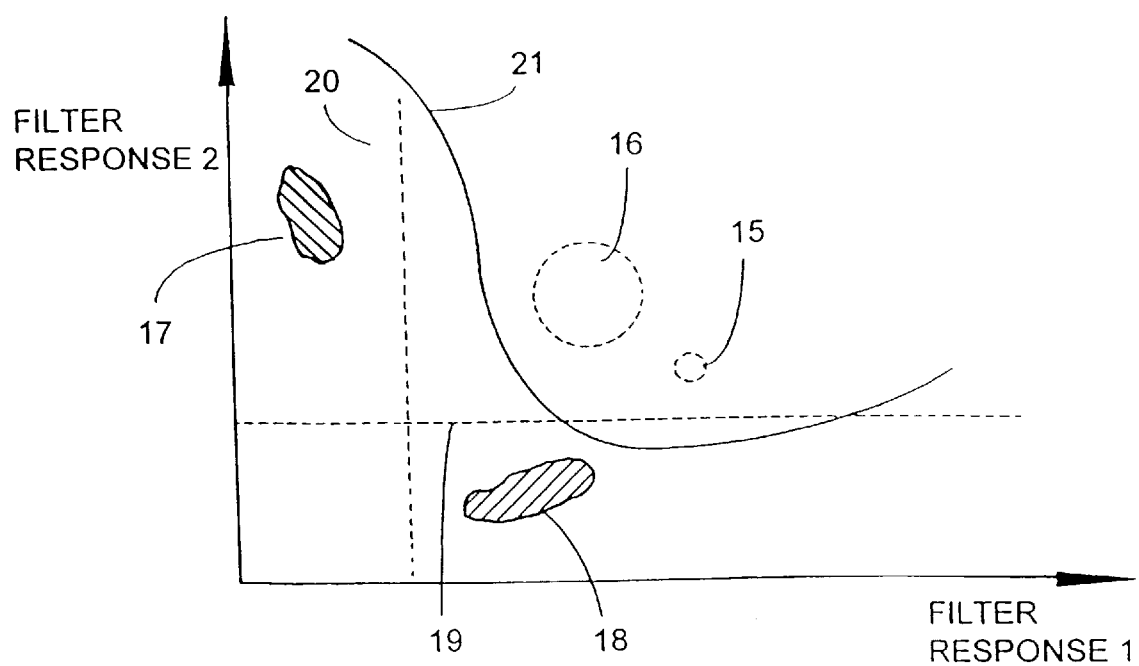
FIG. 9 shows the results of the evaluating method according to FIG. 8.

As is shown in FIG. 9, a sufficient separation of good zones from defect zones has been achieved by using filters 13 and 14 so that good zones and defect zones can now be separated in binary form by introducing thresholds 19, 20 or a separation function 21. The results are the contents of a second storage in the form of a lookup table, which storage is now programmable in two dimensions.

The threshold values can be optimized either by checking the results on a monitor or by means of teaching algorithms. A closest-neighbor classifier, back-propagation network or a maximum likelihood classifier can advantageously be used as teaching algorithms. This is particularly advantageous when the feature space contains structures which are more complex and whose separation can only be effected by a nonlinear separating function. The second storage represents a second classifier by which the intermediate image can be converted into a binary-rendered defect image according to FIG. 10 in which there remain only defects C and D.

In the arrangement for detecting defects in the inspection of structured surfaces shown in FIG. 11, a first classifier KL1 designed as a lookup table in the form of a RAM module is connected by its signal outputs to the inputs of two line buffers ZP1 and ZP2, an image arriving in a point-by-point manner being present at its input. Line buffer ZP1 is connected with a Gauss filter GF on the output side, while line buffer ZP2 is connected with a spot filter SPF whose core represents the second derivative of a two-dimensional Gaussian function. Finally, each filter GF, SPF is connected to an input of a second classifier KL2 which is formed as a two-dimensional lookup table.

Via the first classifier KL1, whose lookup table entries correspond to function f(g) after the teaching phase, the image arriving in a point-by-point manner, as input signal B1, addresses an output signal B2 for conversion of the arriving image into the intermediate image. The output signal B2 is given to line buffer ZP1 and line buffer ZP2 which ensure that the respective image point and its surroundings are sent to filters GF and SPF at the same time.

Figure 10:
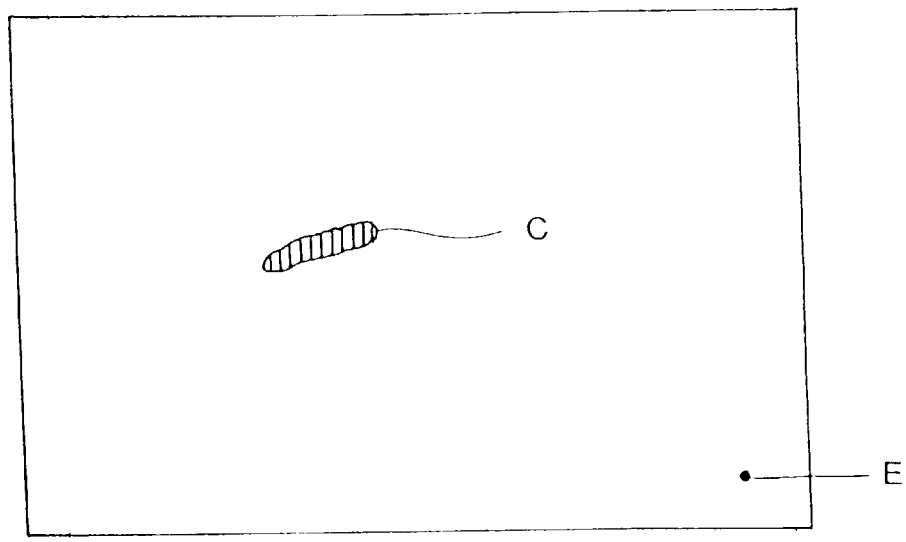
FIG. 10 shows a defect image as results of the method according to the invention.

Filter responses 1 and 2 of filters GF and SPF address the second classifier KL2 as output signals B3 and B4. An output signal B5 containing the defect image corresponding to FIG. 10 is obtained in this way. Signal B5 can be used for displaying on a monitor or is fed to an event receiver. The pipeline structure of the circuit arrangement corresponding to FIG. 11 allows a defect detection in real time with respect to the picture rate.

In the inspection phase, selected inspection zones can now be rastered by image field in video real time. Every image field, e.g., with 512*512 image points, is evaluated point by point by the two classifiers. There results a list of defects with their coordinates for every image field, from which a defect rate can be determined.

An expanded method for determining the contents of the first and second storage when the structure to be inspected cannot be detected by means of an image recording is described with reference to FIGS. 12A and 12B. Two image cutouts BA1, BA2 are selected as test zones from two inspection zones IG1, IG2, each image cutout BA1, BA2 containing a realization of a structure to be analyzed. Whereas the size of the test zones corresponds to the size of a recorded image, the size of the inspection zone is not limited. As has already been described, the contents of the first and second storage are determined with reference to the image cutout BA1. The inspection zone IG1 is then completely processed, wherein the defects with their coordinates are detected in inspection zone IG1.

If it is assumed that defects are rare occurrences, the storage contents can be corrected, as the case may be, by means of a direct evaluation of detected defects. The inspection zone IG2 and other identical zones can then be analyzed for defects.

Image cutout BA2 serves to verify the validity of the storage contents obtained for inspection zone IG1 for inspection zone IG2 by comparing structure features.

While the foregoing description and drawings represent the preferred embodiments of the present invention, it will be obvious to those skilled in the art that various changes and modifications may be made therein without departing from the true spirit and scope of the present invention.

What is claimed is:

1. In a method for detecting defects in inspecting structured surfaces, in particular masks, LCD's, printed circuit boards and semiconductor wafers, using specific image point features of structures and defects of a recorded image of a surface in which zones of the image having similar image point features are compiled by image point classification and a behavior of image point features of an image point is analyzed with reference to its neighboring image points by structure classification, the improvement comprising the step of:

generating a gray-value intermediate image containing edge structures and corner structures and serving for structure classification in an image point classification of the recorded image, the generating of the intermediate image including a step of describing distributions of image point features of selected random samples which correspond at least to a number of defect-free surface portions with distinct features in a feature space plotted by a number of image point features by means of probabilities which are transformed into grayscale values.

2. The method according to claim 1, wherein the grayscale values are contents of a first addressable storage for revaluation of every image point feature of the recorded image into a grayscale value and distributions of all random samples form an overall distribution, the method further comprising storing results of an evaluation of surroundings for each image point of the intermediate image carried out on a basis of at least two uncorrelated characteristics in a second addressable storage in binary form so as to be separated into defect-free regions and defect regions, wherein size of the second addressable storage is determined by a second feature space plotted by a number of evaluated characteristics and the storing in the second addressable storage corresponds to a distribution of characteristics of every image point in the second feature space.

3. The method according to claim 2, including the step of taking the random samples from the recorded image.

4. The method according to claim 2, including the step of taking the random samples from stored image contents.

5. The method according to claim 2, including the step of taking the random samples from the recorded image as well as from the stored image contents.

6. The method according to claim 2, including the step of using random samples of surface portions with defects in addition to the selected random samples which correspond at least to the number of defect-free surface portions with distinct features.

7. The method according to claim 2, including the step of effecting the evaluation of surroundings by at least two filters with variable core and uncorrelated characteristics by noise suppression and highlighting self-contained zones lying within the evaluated surroundings.

8. The method according to claim 7, including the step of moving a pair of filters, one of said pair being a low-pass filter and the other being a bandpass filter.

9. The method according to claim 8, including the step of using a Gauss filter as the low-pass filter and a spot filter as the bandpass filter whose core is a second derivative of a two-dimensional Gaussian function.

10. The method according to claim 9, including the step of using lookup tables as addressable storages.

11. The method according to claim 10, including the step of using color features of the image points as image point features.

12. The method according to claim 10, including the step of using texture features which are associated with each image point by its surroundings as image point features.

13. The method according to claim 11, including the steps of first selecting an image cutout which corresponds to dimensions of the recorded image and in which detected defects once again serve as random samples from a first inspection zone of different inspection zones in order to determine contents of the first addressable storage and the second addressable storage and testing applicability of results of the contents determination to at least one image cutout in at least one of the different inspection zones other than the first inspection zone.

14. The method according to claim 12, including the steps of first selecting an image cutout which corresponds to dimensions of the recorded image and in which detected defects once again serve as random samples from a first inspection zone of different inspection zones in order to determine contents of the first addressable storage and the second addressable storage and testing applicability of results of the contents determination to at least one image cutout in at least one of the different inspection zones other than the first inspection zone.

15. In a method for detecting defects in inspecting structured surfaces, in particular masks, LCD's, printed circuit boards and semiconductor wafers, using specific image point features of structures and defects of a recorded image of a surface in which zones of the image having similar image point features are compiled by image point classification and a behavior of image point features of an image point is analyzed with reference to its neighboring image points by structure classification, the improvement comprising the step of:

generating a gray-value intermediate image containing edge structures and corner structures and serving for structure classification in an image point classification of the recorded image, the generating of the intermediate image including a step of describing separate continuous distributions of image point features of randomly selected sample regions of the recorded image which correspond at least to a number of defect-free surface portions with distinct features in a feature space, the generating of the intermediate image further including steps of approximating each of the separate continuous distributions by a respective probability function that is normalized to 1, calculating an overall probability function for any image point feature to be present in any one of the structures by use of all the probability functions of the separate continuous distributions and transforming each image point feature into a grayscale value by the overall probability function.

16. The method according to claim 15, wherein the grayscale values are contents of a first addressable storage for revaluation of every image point feature of the recorded image into a grayscale value and distributions of all randomly selected sample regions form an overall distribution, the method further comprising storing results of an evaluation of surroundings for each image point of the intermediate image carried out on a basis of at least two uncorrelated characteristics in a second addressable storage in binary form so as to be separated into defect-free regions and defect regions, wherein size of the second addressable storage is determined by a second feature space plotted by a number of evaluated characteristics and the storing in the second addressable storage corresponds to a distribution of characteristics of every image point in the second feature space.

17. The method according to claim 16, including the step of taking the randomly selected sample regions from the recorded image.

18. The method according to claim 16, including the step of taking the randomly selected sample regions from stored image contents.

19. The method according to claim 16, including the step of taking the randomly selected sample regions from the recorded image as well as from stored image contents.

20. The method according to claim 16, including the step of using random samples of surface portions with defects in addition to the randomly selected sample regions which correspond at least to the number of defect-free surface portions with distinct features.

21. The method according to claim 16, further including the step of effecting the evaluation of surroundings by at least two filters with variable core and uncorrelated characteristics by noise suppression and highlighting self-contained zones lying within the evaluated surroundings.

22. The method according to claim 21, including the step of moving a pair of filters, one of said pair being a low-pass filter and the other being a bandpass filter.

* * * * *